United States Patent
Parks

(10) Patent No.: US 6,433,006 B2
(45) Date of Patent: *Aug. 13, 2002

(54) METHOD OF TREATMENT OF SEBORRHEIC DERMATITIS

(76) Inventor: L. Dean Parks, 2420 SE. 15th St., Ocala, FL (US) 34471

( * ) Notice: Subject to any disclaimer, the term of this patent is extended or adjusted under 35 U.S.C. 154(b) by 0 days.

This patent is subject to a terminal disclaimer.

(21) Appl. No.: 09/976,914

(22) Filed: Oct. 12, 2001

Related U.S. Application Data

(63) Continuation of application No. 09/605,747, filed on Jun. 29, 2000, now Pat. No. 6,319,945.

(51) Int. Cl.⁷ ............................................. A61K 31/35
(52) U.S. Cl. ...................................... 514/453; 514/859
(58) Field of Search ................................ 514/453, 859

(56) References Cited

U.S. PATENT DOCUMENTS

| | | | |
|---|---|---|---|
| 5,654,312 A | * | 8/1997 | Andrulis, Jr. et al. |
| 5,728,719 A | * | 3/1998 | Miller |
| 5,786,344 A | * | 7/1998 | Ratain et al. |
| 5,789,191 A | * | 8/1998 | Mayer et al. |
| 5,877,295 A | * | 3/1999 | Diamond et al. |
| 5,952,372 A | * | 9/1999 | Mcdaniel |
| 6,136,806 A | * | 10/2000 | Hittel |

OTHER PUBLICATIONS

Darge, et al. Ivermectin treatment of hyperactive onchodermatitis . . . , Database Caplus, abstract Trp. Med. Parasitol., 1995, vol. 46/4, pp. 206–212.*

Osamulia et al., Psoriasis and filariasis, British J. of Derm, 1994. Report form 266th NSDV meeting, pp. 723–724.*

Seavers, A., Cutaneous syndrome possibly caused by heartworm infestation in a dog, Aust. Vet. J. 1998, vol. 76/1, pp. 18–20.*

Rook, et al., Textbook of Dermatology, @nd edition, 1968, pp. 154 and 263.*

* cited by examiner

Primary Examiner—William R. A. Jarvis
Assistant Examiner—Vickie Kim
(74) Attorney, Agent, or Firm—M. K. Silverman; Yi Li

(57) ABSTRACT

A method of treatment of seborrheic dermatitis includes the application, in the form of either a lotion or a cream, of a mixture including a therapeutically effective amount of ivermectin in water preferably in a concentration of about 750 micrograms per milliliter (mcg/ml), in the case of a lotion, and with a pharmaceutically acceptable carrier if used as a cream. Such a lotion or cream is applied nightly preferably for a period of seven days and then employed on a maintenance basis one to four times per month.

6 Claims, No Drawings

METHOD OF TREATMENT OF SEBORRHEIC DERMATITIS

REFERENCE TO RELATED APPLICATION

This case is a continuation of application Ser. No. 09/605,747, U.S. Pat. No. 6,319,945 filed Jun. 29, 2000.

BACKGROUND OF THE INVENTION

Seborrheic dermatitis, also known as seborrheic eczema and seborrhea, is a chronic superficial inflammatory disease of the skin capable of affecting many parts of the body including the scalp, eyebrows, nasolabial creases, lips, ears, sternal area, axillae, submammary folds, umbilicus, groins, and gluteul crease. The disease is characterized by many shapes, sizes, and surface textures and is often crust-like, yellowish, and accompanied by itching. This is also characterized by remission and exacerbation.

The etiology, pathogenesis and histology of seborrheic dermatitis is unresolved. However, it bears close clinical resemblance to psoriasis and many researchers are of the belief that both conditions share a related etiology, notwithstanding that psoriasis is a broader and less definable condition. Therein, psoriasis typically differentiates over seborrheic dermatitis in its absence of itching and its resistance treatment by compounds, such as, selenium sulfide and zinc pyrithione which have been employed in the treatment of seborrheic conditions.

Some researchers attribute seborrheic dermatitis to a zinc deficiency while others consider its etiology to be microbial. Yet others believe that a hormonal influence exists since the condition does not appear before puberty. It has also been hypothesized that a specific fungus, i.e., a lipophiolic plemorphic the fungus is responsible for various forms of seborrheic dermatitis. As such, the argument that yeast, a common form of such fungus, is at least one cause of such dermatitis, is considered a persuasive one.

Prior art which reflects the view that seborrheic dermatitis is a zinc deficiency is reflected in U.S. Pat. No. 5,997,852 (1999) to Akiko, et al, entitled Remedy For Dermatitis, while the school that views seborrheic dermatitis as microbial in origin and, thereby, urges treatment of the same with antibiotics, is reflected in U.S. Pat. No. 4,965,935 (1986) to Rosenberg, et al entitled Topical Treatment Of Psoriasis With Imidazole Antibiotics. As such, Rosenberg, et al equates pathogenic psoriasis with pathogenic seborrheic dermatitis. In this view of the condition, it is also common to employ polymycin B-hydrocortisone, i.e., a cortisone-medicated antibiotic, as a topical liquid.

The instant invention derives from the school which views soborrheic dermatitis as essentially fungal and, as such, caused by organisms at the largest end of the spectrum of microscopic organisms. That is, organisms larger than bacteria, but is still not visible to human eye. These include as yet undetected microorganisms, amenable or responsive to treatment with topical ivermectin.

SUMMARY OF THE INVENTION

The present invention constitutes a method of treatment of seborrheic dermatitis consisting of the application, in the form of either a lotion or a cream, of a mixture comprising a therapeutically effective amount of ivermectin in water in a concentration of about 750 micrograms per milliliter (mcg/ml), in the case of a lotion, and with a pharmaceutically acceptable carrier if used as a cream. Such a lotion or cream is applied nightly for a period of seven days and then employed on a maintenance basis one to four times per month.

It is accordingly an object of the invention to provide a curative topical therapy for the treatment of seborrheic dermatitis.

It is another object to provide a safe and effective method for the treatment of such dermatitis which will afford a substantially permanent relief therefrom.

The above and yet other objects and advantages of the present invention will become apparent from the hereinafter set forth Detailed Description of the Invention and claims appended herewith.

DETAILED DESCRIPTION OF THE INVENTION

The inventive topical use of ivermectin, which is a part of a larger chemical family known as avermectins, has historically been a product of Merck & Co., Inc., Rahway, N.J.

It is known to one skilled in the art that ivermectin is one of compounds of avermectin family. In fact, ivermectin is also called 22, 23-dihydroavermectin $B_1$ as shown in the Merck Index (Eleventh Edition, pages 825–826, see attached copy). Furthermore, the relationship between ivermectin and avermectins is also indicated in the definition of avermectins in the Merck Index (Eleventh Edition, pages 140–141). It has historically been employed in veterinary applications for the treatment of endoparasitic conditions in animals. However, some medical papers, particularly from the third world and tropical regions, have suggested that the use of ivermectin in humans in the treatment of internal or endoparasatic conditions, such as myiasis and onchocerciasis. However, these conditions have no known pathogenic or histologic connection to seborrheic dermatitis or, for that matter, to any known form of psoriasis. Further, no publication known to the within inventor has ever suggested employment of topical ivermectin in the treatment of any form of dermatitis.

The instant invention entails the use of a therapeutically effective quantity of ivermectin, generally available from Merck as a paste, which, when dissolved in water, is sufficient to form a lotion having a concentration of at least 750 mcg per ml. Alternatively, a cream of ivermectin may be formed, this in combination with a pharmaceutically acceptable carrier such as propylene glycol, sodium lauryl sulfate, zanthan gum, or combinations thereof.

The lotion or cream is then applied on a daily basis for seven days and, thereafter, one to four times per month on the affected area to prevent recurrence of the condition.

With respect to mechanism of action, it is believed that the effect of ivermectin upon the skin relates principally to sebaceous glands which exist in almost every follicule of the human skin, and are vulnerable to attack by fungii. Accordingly, therein the fungus theory as well as the hormonal dysfunction theory of seborrheic dermatitis is addressed. Also, due to the relaxation effect on the skin which has been demonstrated in the application thereto of ivermectin, the theory of etiology relative to emotional stress and associated increased perspiration as a cause of seborrheic dermatitis, is also addressed. As such, the quieting and desensitizing effect of ivermectin is believed to subdue the motor lability to thereby reduce capillary stress associated with the condition.

Over a period of experimental testing of about seven years upon about 100 patients in my practice in Ormond Beach, Fla., I found results of the above method to be both safe and remarkably effective in the treatment of otherwise stubborn conditions of seborrheic dermatitis. Further, where the patients have followed the proper regime of use of ivermectin, I have seen no recurrence of the condition. Also, none of the side effects, such as allergic irritation or burning, associated with prior art medication, particularly, topical antibiotics have appeared. Thereby, in my use of the above described ivemectin lotion and cream, I have not encountered any auto immune response from patients so treated as, occasionally, has been case with the using antibiotics such as erythromycin, tetracycline, and imidazoles such as ketanazole. Accordingly, I believe I have discovered an effective and almost universally safe method of the treatment of seborrheic dermatitis which may have additional value in the treatment of types of psoriasis having an etiology common to seborrheic dermatitis.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

Having thus described my invention, what I claim as new, useful and non-obvious and, accordingly, secure by Letters Patent of the United States is:

1. A method of treating seborrheic dermatitis comprising topically applying a therapeutically effective amount of ivermectin to an affected area of a human patient.

2. The method of claim 1, wherein said ivermectin is in a pharmaceutically acceptable carrier.

3. The method of claim 2, wherein said ivermectin is in a concentration of no less than 750 mcg/ml.

4. The method of claim 2, wherein said pharmaceutically acceptable carrier comprises water, propylene glycol, sodium lauryl sulfate, xanthum gum, and combinations thereof.

5. The method of claim 4, wherein said ivermectin in a pharmaceutically acceptable carrier is in a form of lotion or cream.

6. The method of claim 1, wherein said topically applying a therapeutically effective amount of ivermectin to said affected area of said patient comprising the steps of:

(a) topically applying said ivermectin daily for a period of about seven days, and (b) topically applying said ivermectin one to four times per month for a period of several months.

* * * * *